(12) United States Patent
Palaniappan (10) Patent No.: US 8,507,197 B2
(45) Date of Patent: Aug. 13, 2013

(54) QUALITY CONTROL METHODS FOR ARRAYED OLIGONUCLEOTIDES

(75) Inventor: Chockalingam Palaniappan, Eugene, OR (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 1187 days.

(21) Appl. No.: 12/063,444

(22) PCT Filed: Jul. 27, 2006

(86) PCT No.: PCT/US2006/029524
§ 371 (c)(1),
(2), (4) Date: Feb. 11, 2008

(87) PCT Pub. No.: WO2007/021502
PCT Pub. Date: Feb. 22, 2007

(65) Prior Publication Data
US 2009/0143234 A1    Jun. 4, 2009

Related U.S. Application Data

(60) Provisional application No. 60/706,949, filed on Aug. 10, 2005.

(51) Int. Cl.
*C12Q 1/68* (2006.01)
*C07H 21/04* (2006.01)
*C12M 1/36* (2006.01)

(52) U.S. Cl.
USPC ........ 435/6.1; 435/6.11; 435/287.2; 536/23.1

(58) Field of Classification Search
None
See application file for complete search history.

(56) References Cited

U.S. PATENT DOCUMENTS

| 4,851,331 | A  * | 7/1989  | Vary et al. ................... 435/6 |
| 6,714,299 | B2   | 3/2004  | Peterson et al. |
| 6,986,992 | B2   | 1/2006  | Chui et al. |
| 2001/0051712 | A1 * | 12/2001 | Drysdale et al. ............ 536/23.5 |
| 2001/0051715 | A1 * | 12/2001 | Taylor et al. ................ 536/25.4 |
| 2003/0008312 | A1 * | 1/2003  | Gill et al. .................... 435/6 |
| 2003/0020910 | A1   | 1/2003  | Peterson et al. |
| 2004/0018506 | A1 * | 1/2004  | Koehler et al. .............. 435/6 |
| 2004/0235022 | A1   | 11/2004 | Mauritz et al. |

FOREIGN PATENT DOCUMENTS

| WO | 96/31622 | 10/1996 |
| WO | 2004/003233 | 1/2004 |
| WO | 2005/003304 | 1/2005 |

OTHER PUBLICATIONS

Syvanen, A., "From Gels to Chips: 'Minisequencing' Primer Extension for Analysis of Point Mutations and Single Nucleotide Polymorphisms". Human Mutation, 13:1-10 (1999).

* cited by examiner

*Primary Examiner* — Betty Forman (57) ABSTRACT

We disclose quality controls methods that allow quick and accurate verification of a test oligonucleotide deposited on a solid support. It is especially useful for the verification of oligonucleotides representing alleles of a multi-allelic locus. It employs single base extension, with labeled dideoxynucleotides, to locate and verify the identity of test oligonucleotides. This approach involves synthesizing a complement probe oligonucleotide for each oligonucleotide being tested. Probe oligonucleotides are optionally grouped. They are then hybridized to test oligonucleotides, and the hybridized pair is subject to single base extension and detection. It requires the presence of one unique base, either in the last two bases at the free hanging end of the test oligonucleotide—as opposed to the end anchored to the solid support surface, or in the last two bases at one end of the probe oligonucleotide.

7 Claims, 8 Drawing Sheets

QUALITY CONTROL METHODS FOR ARRAYED OLIGONUCLEOTIDES

CROSS-REFERENCE TO RELATED APPLICATIONS

This application is a filing under 35 U.S.C. §371 and claims priority to international patent application number PCT/US2006/029524 filed Jul. 27, 2006, published on Feb. 22, 2007, as WO 2007/021502, which claims priority to U.S. provisional patent application No. 60/706,949 filed Aug. 10, 2005; the entire disclosure of which is incorporated herein by reference in its entirety.

FIELD OF THE INVENTION

The present invention relates to a quality control method for oligonucleotides on a solid support. More specifically, the invention relates to the use of single base extension and detection to verify the identity of oligonucleotides attached to a solid support.

BACKGROUND OF THE INVENTION

The genomic revolution is fundamentally changing today's medical practice. Disease biomarkers have been identified for multiple human diseases, and this opened up the filed of molecular diagnostics. Genomics based biomarkers are being used for diagnosing a number of conditions, as well as directing the proper therapeutics regimen for others. Some of these genomics biomarkers are gene expression signatures, while others are genotype/haplotype based signatures, including single nucleotide polymorphisms. New signatures are rapidly been identified for more diseases and conditions.

High throughput DNA analysis such as DNA microarrays based assays play an important role in biomarker discovery as well as diagnostics and disease monitoring. It has and will continue to make substantial contributions to the medical field, enabling the transition of medical practice from the current late disease model to an early health model, in that disease prevention plays an ever increasingly important role in the new era of personalized healthcare.

Oligonucleotide based microarray platform is rapidly becoming a preferred platform for biomarker discovery and molecular diagnostics. Recently, Roche AMPLICHIP™ Cytochrome P450 Genotyping test and Affymetrix GENE-CHIP™ Microarray Instrumentation System was cleared to enter the US and European market, for use to help a clinician determine if a patient has mutations in their CYP450 2D6 gene that may affect their ability to metabolize certain drugs. It is anticipated that additional, similar platforms will enter the market.

Increasingly, it is found that a small number of genes/signatures are enough for diagnosis of a certain disease or condition. In these instances, it is possible to use a bead based platform, for the discovery and diagnostics. Platform such as the XMAP™ technology from Luminex Corporation is one such example. XMAP™ uses color-codes tiny beads, called microspheres, and up to 100 distinct assay reactions can be multiplexed in a single volume.

Quality assurance for nucleic acid fragments used in these assays, especially oligonucleotides, is a key to the success of the system. U.S. Pat. No. 6,714,299 describes the use of light scattering particles in the quality control of microscale devices including microarrays. U.S. patent application Ser. No. 10/802,249, published as US2004-0235022, discloses a quality control method for the on-chip synthesis of biopolymer arrays, with the use of detectable protecting groups. However, there is currently no effective method for the quality control/assurance for oligonucleotides deposited on a microarray or bead, especially for arrays or beads produced in a high volume.

BRIEF DESCRIPTION OF THE INVENTION

Here we provide a quality control approach that allows quick and accurate verification of a test oligonucleotide deposited on a solid support. It is especially useful for the verification of oligonucleotides representing alleles of a multi-allelic locus. It employs single base extension, with labeled dideoxynucleotides, to locate and verify the identity of the test oligonucleotides. This approach involves synthesizing a complement probe oligonucleotide for each oligonucleotide being tested. Probe oligonucleotides are optionally grouped. They are then hybridized to test oligonucleotides, and the hybridized pair is subject to single base extension and detection. It requires the presence of one unique base, either in the last two bases at the free hanging end of the test oligonucleotide (as opposed to the end anchored to the solid support surface), or in the last two bases at one end of the probe oligonucleotide.

DETAILED DESCRIPTION OF THE INVENTION

Figure 1:
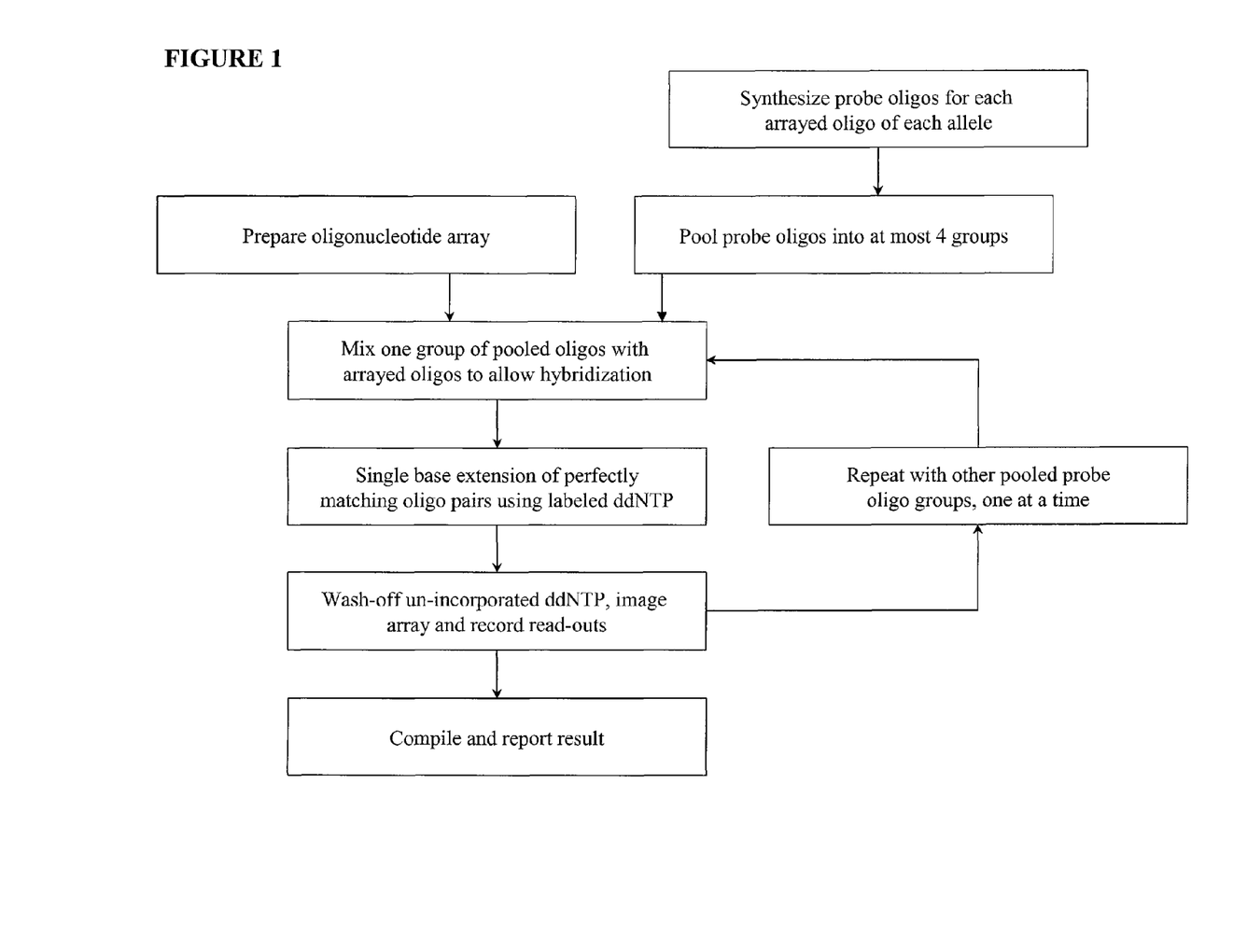
FIG. 1 shows a flow chart for the method of verification of oligonucleotides on a solid support in an array format.

We describe here methods for verification of the identity of oligonucleotides using an approach that involves single nucleotide extension, by a polymerase reaction, with dye or hapten labeled-ddNTP on a solid support. The method involves anchoring the test oligonucleotides on a solid support, preferably in an array format; hybridizing with complement probe oligonucleotides; performing single base extension reactions with labeled dideoxynucleotides; and detecting the label. The absence of a detectable label at a particular location or bead is indicative of a poor quality test oligonucleotide at that location or bead. Depending on the orientation of the anchored test oligonucleotides, slight variations of the method are envisioned, including separation of probe oligonucleotides into groups, whereas probes for each allele of a multi-allelic locus is separated into a different group. FIG. 1 shows a high level overview of the method in an array format, either on a slide or a membrane.

In one embodiment, the invention provides a method for the verification of identity of oligonucleotides on a solid support, comprising: (a) preparing an array of test oligonucleotides on the solid support, whereas each of the test oligonucleotides is anchored at the 5' end and occupies a predetermined location on the solid support, and whereas test oligonucleotides for each allele of a multi-allelic locus occupies a separate location and the last base at the 3' end is unique to the allele of the multi-allelic locus; (b) synthesizing probe oligonucleotides for each arrayed test oligonucleotide, the probe oligonucleotides being a complement of the arrayed test oligonucleotide and contain one additional base at the 5' end; (c) pooling the probe oligonucleotides into at most four groups, wherein probe oligonucleotides representing each allele of a multi-allelic locus is separated into a different group; (d) mixing one group of pooled probe oligonucleotides with the arrayed test oligonucleotides to allow hybridization of probe and test oligonucleotides on the solid support; (e) performing single base extension reaction with labeled ddNTP, wherein extension occurs only for those test oligonucleotides having a 3' base that hybridizes with a probe oligonucleotide; (f) washing off ddNTP not incorporated into test oligonucleotides; (g) detecting labels on extended test oligonucleotides and their location; (h) repeating steps d. through g. for each additional group of pooled probe oligonucleotides; (i) predicting locations where a label is added to the test oligonucleotide, based on pooling information and probe oligonucleotide sequence information; (j) comparing detected labels and location information from step h. with the predicted test oligonucleotide location information from step i., whereas any non-match is indicative of a poor quality of the test oligonucleotide at that location. Optionally, a report is generated containing a list of test oligonucleotides that is of poor quality.

Figure 2:
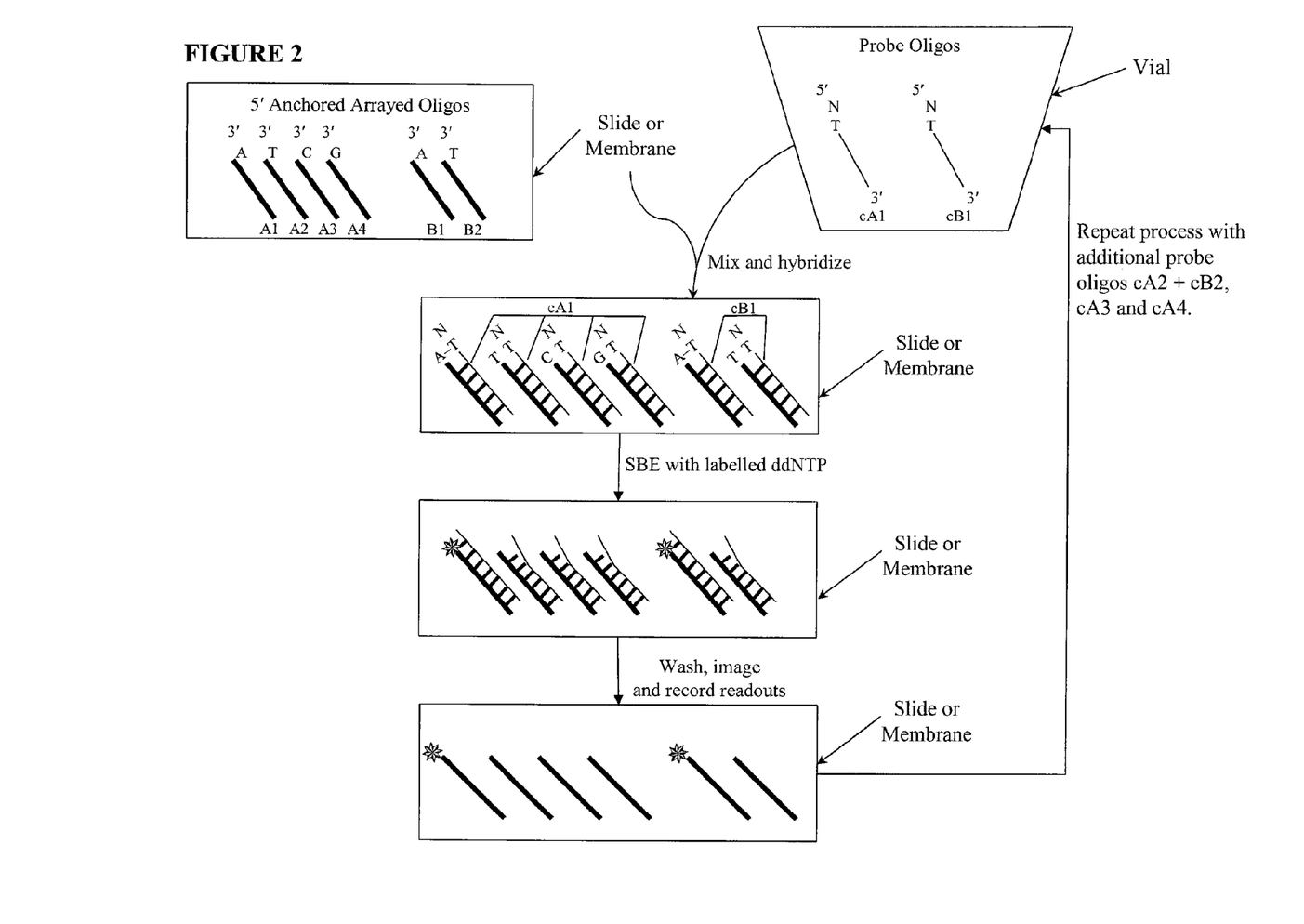
FIG. 2 illustrates one scheme for the method of verification of oligonucleotides on a solid support. Arrayed oligonucleotides have their 5' ends anchored to the surface of the slide. The last base at the 3' end of the arrayed oligonucleotides is unique and represents each allele (A1-A4, and B1-B2, respectively) of a multi-allelic locus. Arrayed oligonucleotides are only extended at the presence of a perfectly matching probe oligonucleotide.

FIG. 2 provides a schematic drawing of the key steps of the above embodiment. Arrayed test oligonucleotides have their 5' ends anchored to the surface of the slide or a membrane. The 3' ends of the arrayed test oligonucleotides are not bound to the surface. As an example, test oligonucleotides from two multi-allelic loci ("A" and "B") are shown here. Locus A has four alleles, represented by oligonucleotides A1, A2, A3 and A4. These four alleles only differ by their last base at the 3' end, each represents one naturally occurring base (A, T, C, G respectively). Locus B has two alleles, represented by oligonucleotides B1 and B2. These alleles also only differ by the 3' most base, each represents one naturally occurring base of the two alleles (as an example, A, T, respectively). Complement probe oligonucleotides are synthesized for each allele (cA1-cA4 and cB1, cB2, c stands for complement). Each of the probe oligonucleotides is a complement to an arrayed test oligonucleotide, with an additional base at the 5' end. For example, cA1 has a T at the second base at the 5' end, while cB1 also has a T at the second base at the 5' end. The probe oligonucleotides are pooled into four groups (cA1 and cB1, cA2 and cB2, cA3, cA4, respectively). Each group is analyzed by hybridization, allele specific single base extension (SBE) with labeled ddNTP, and imaging analysis. As an example, when cA1 and cB1 are mixed and hybridized with the arrayed test oligonucleotides, a perfect match occurs between A1 and cA1, as well as B1 and cB1, as indicated by a short line connecting the two oligonucleotide strands. Note that the number of connecting lines does not directly correspond to the length of the oligonucleotide—they are for illustration only. Although cA1 might hybridize with A2, A3 or A4, only A1 matches cA1 at the 3' end, allowing SBE and labeling of A1. For the same reason, B 1 is also labeled, but not B2. When the unincorporated ddNTP are washed off, imaging of the slide or membrane provides information on the locations of labeled test oligonucleotides. In the same time, a prediction is made, most likely by a computer algorithm, as to the expected locations of labels on the surface, based on the test and probe oligonucleotide combination and sequence and location information. This prediction is compared with the location information from the imaging results. A perfect match is indicative of a good quality test oligonucleotide, while a non-match indicates a poor quality oligonucleotide at the test location. Cycling of this process with additional probe oligonucleotide groups (cA2 and cB2, cA3, cA4, respectively) enables verification of all test oligonucleotides.

A slight variation of the example shown in FIG. 2 only requires a single dideoxynucleotide for the SBE, not all four ddNTP. Here, all the probe oligonucleotides within each pooled group are designed to contain the same base at the 5' end. For example, the 5' base of cA1 and cB1 are both the same, not a random base N as shown in the Figure. This way, only a single, complementary, labeled dideoxynucleotide is needed for the SBE reaction. Imaging of the labels is also simplified as only a single kind of label is present on the surface after SBE. This simplifies the SBE reaction and the subsequent imaging process.

In another embodiment, the invention provides a method for the verification of identity of oligonucleotides on a solid support, comprising: (a) preparing an array of test oligonucleotides on the solid support, whereas each of the test oligonucleotides is anchored at the 5' end and occupies a predetermined location on the solid support, and whereas test oligonucleotides for each allele of a multi-allelic locus occupies a separate location and the last base at the 3' end is unique to the allele of the multi-allelic locus; (b) synthesizing probe oligonucleotides for each arrayed test oligonucleotide, the probe oligonucleotides being a complement of the arrayed test oligonucleotide and contain one additional base at the 5' end, the additional base being distinct for each allele of a multi-allelic locus; (c) mixing probe oligonucleotides with the arrayed test oligonucleotides to allow hybridization of probe and test oligonucleotides on the solid support; (d) performing single base extension reaction with distinctly labeled ddNTP, wherein extension occurs only for those test oligonucleotides having a 3' base that hybridizes with a probe oligonucleotide; (e) washing off ddNTP not incorporated into test oligonucleotides; (f) detecting labels on extended test oligonucleotides and their location; (g) predicting for each location, the label that should be present, based on information of the distinct label for the complement dideoxynucleotide to the 5' base of the probe oligonucleotide; (h) comparing the detected labels and location information from step f. with predicted label information from step g., whereas any non-match is indicative of a poor quality of the test oligonucleotide at that location. Optionally, a report is generated containing a list of test oligonucleotides that is of poor quality.

Figure 3:
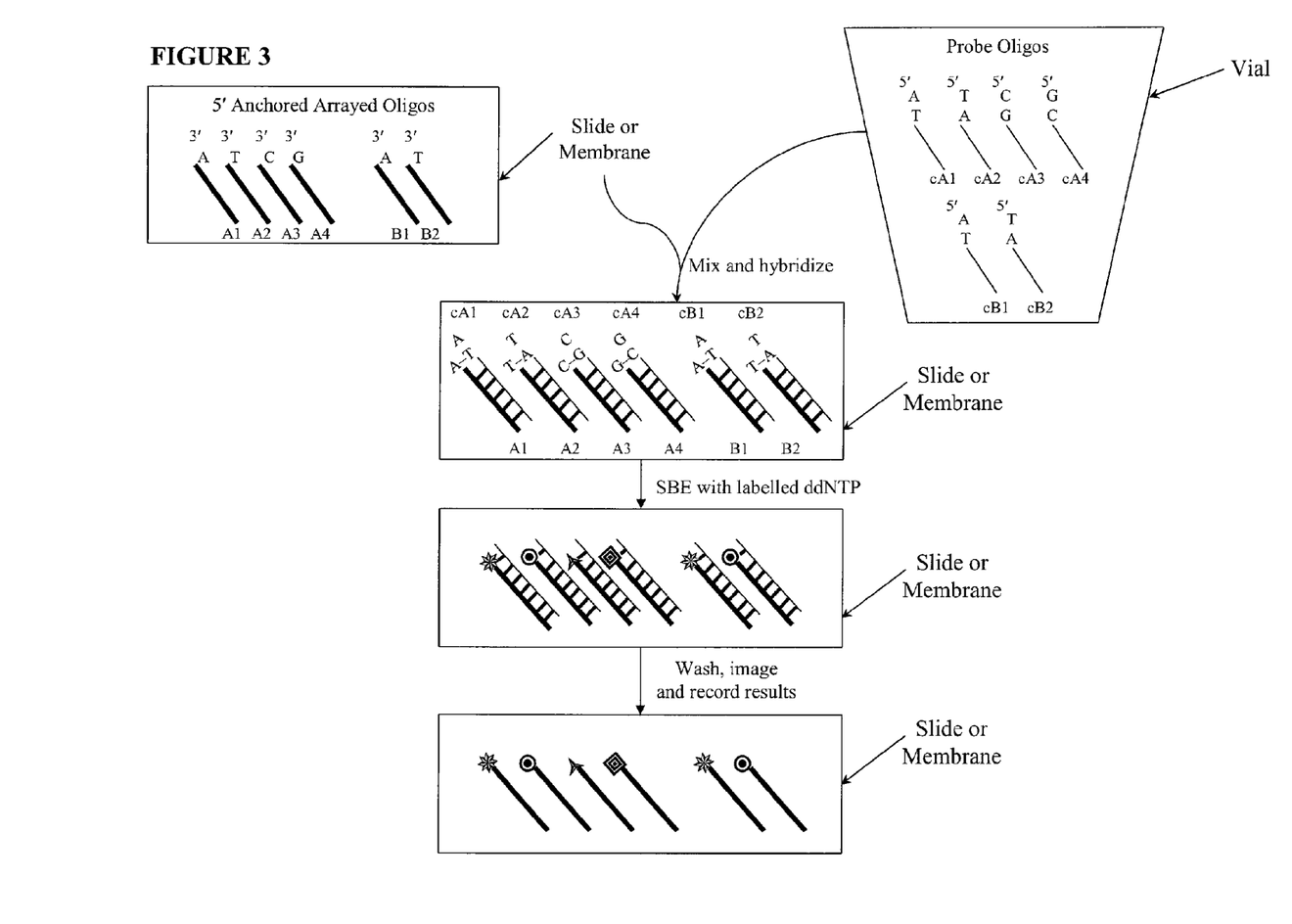
FIG. 3 illustrates a variant of the scheme of FIG. 2. The last base at the 3' end of the arrayed oligonucleotides is unique and represents each allele (A1-A4, and B1-B2, respectively). The last base at the 5' end of the probe oligonucleotides is designed to be unique for each allele as well (cA1-cA4, and cB1-cB2, respectively). The ddNTP are distinctly labeled. Each arrayed oligonucleotide from a multi-allelic locus acquires a distinct label after the allele specific, single base extension.

FIG. 3 provides a schematic drawing of the key steps of the above embodiment. It is a variation of the embodiment represented by FIG. 2, with some modifications. Here the several (one to four) probe oligonucleotides for each loci are designed to contain a different 5' base. For example, the last base at the 5' end of cA1, cA2, cA3 and cA4 are A, T, C, G, respectively. The last base at the 5' end of cB1, cB2 are A, T, respectively. Grouping of the probe oligonucleotides are not necessary here. Instead, all the probe oligonucleotides are pooled together for hybridization and SBE reaction. Although there is potential cross hybridization of probe oligonucleotides (cA2, cA3, cA4 hybridize with A1), only perfectly matching probe/test pair will result in extension (e.g., extension of a T for A1). The use of distinctly labeled ddNTP ensures a distinct label for each extension product, since the probes carry a different 5' base.

In yet another embodiment, the invention provides a method for the verification of identity of oligonucleotides on a solid support, comprising: (a) preparing an array of test oligonucleotides on the solid support, whereas each of the test oligonucleotides is anchored at the 3' end to, and occupies a predetermined location on the solid support, and whereas test oligonucleotides for each allele of a multi-allelic locus occupies a separate location and the last base at the 5' end is unique to the allele of the multi-allelic locus; (b) synthesizing probe oligonucleotides which are complements of the arrayed test oligonucleotides, wherein for a multi-allelic locus, only one probe is synthesized, and the 3' base of the probe oligonucleotides is a complement to the second base of the test oligonucleotides at the 5' end; (c) mixing probe oligonucleotides with the arrayed test oligonucleotides to allow hybridization of probe and test oligonucleotides on the solid support; (d) performing single base extension reaction with distinctly labeled ddNTP, whereas extension occurs on probe oligonucleotides and each allele of a multi-allelic locus is distinctly labeled; (e) washing off ddNTP not incorporated into probe oligonucleotides; (f) detecting labels on extended probe oligonucleotides and their location; (g) predicting, based on test oligonucleotide location and 5' unique sequence information, expected label for each locations; and comparing the detected labels and location information from step (f) with the predicted label information for each locations from step (g), whereas any non-match is indicative of a poor quality of the test oligonucleotide at that location.

Figure 4:
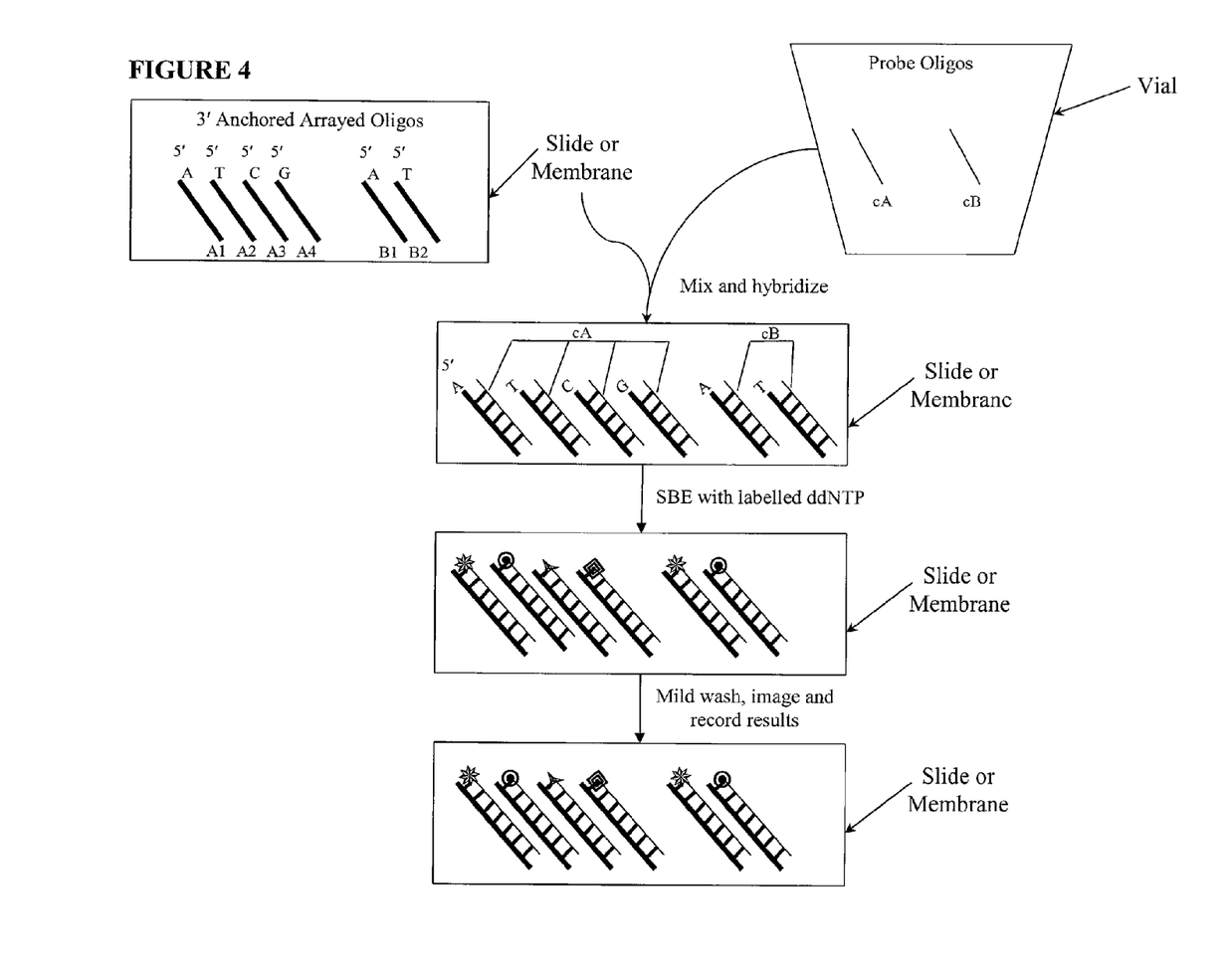
FIG. 4 illustrates an alternative scheme for the method of verification of oligonucleotides on a solid support. Arrayed oligonucleotides have their 3' ends anchored to the surface of the slide. The last base at the 5' end of the arrayed oligonucleotides is unique and represents each allele (A1-A4, and B1-B2, respectively) of a multi-allelic locus. A common probe oligonucleotide is synthesized for each locus. The ddNTP are distinctly labeled. Each arrayed oligonucleotide from a multi-allelic locus acquires a distinct label after the single base extension.

FIG. 4 provides a schematic drawing of the key steps of the above embodiment. It is important to note that here the arrayed test oligonucleotides are anchored via their 3' ends to the surface of the slide or membrane. Therefore, the 5' ends of these oligonucleotides are not bound to the surface. For a multi-allelic locus, each allele is represented by a different test oligonucleotide, and the distinct base is the 5' last base of the oligonucleotide. For example, for locus A, the 5' base of A1, A2, A3, A4 are A, T, C, G, respectively; for locus B, the 5' base of B 1, B2 are A, T, respectively. A common probe oligonucleotide is synthesized for each locus (e.g., cA), with the last base at the 3' end being complement to the second base of the 5' end of the test oligonucleotide on the array. The common probe oligonucleotides for each locus are hybridized to each of the allele specific test oligonucleotides. Single base extension adds a single base to the 3' end of each hybridized probe oligonucleotide. Because the template base (5' base for the test oligonucleotide) is unique for each allele of a locus, the added base on the probe is unique to that allele as well. Using distinctly labeled ddNTP, a unique label is therefore present on extended probe oligonucleotide at each location (at each allele for every locus). The slides or membranes are then washed mildly to get rid of the labeled ddNTP, but to keep hybridized and extended oligonucleotide pairs (probe and test pairs) in place. The distinct labels are imaged, and information on the label and location is compared to the expected results.

In still another embodiment, the invention provides a method for the verification of identity of oligonucleotides on a solid support, comprising: (a) preparing an array of test oligonucleotides on the solid support, whereas each of the test oligonucleotides is anchored at the 3' end and occupies a predetermined location on the solid support, and whereas test oligonucleotides for each allele of a multi-allelic locus occupies a separate location and the second to last base at the 5' end is unique to the allele of the multi-allelic locus; (b) synthesizing probe oligonucleotides for each arrayed test oligonucleotide, the probe oligonucleotides being a complement of the arrayed test oligonucleotide and the 3' last base is a complement to the unique base at the second to last position of the 5' end of the arrayed test oligonucleotide; (c) pooling the probe oligonucleotides into at most four groups, wherein probe oligonucleotides representing each allele of a multi-allelic locus is separated into a different group; (d) mixing one group of pooled probe oligonucleotides with the arrayed test oligonucleotides to allow hybridization of probe and test oligonucleotides on the solid support; (e) performing single base extension reaction with labeled ddNTP, wherein extension occurs only on those probe oligonucleotides the 3' end of which match perfectly with the second base at the 5' end of the arrayed test oligonucleotide; (f) washing off ddNTP not incorporated into probe oligonucleotides; (g) detecting labels on extended probe oligonucleotides and their location; (h) repeating steps (d) through (g) for each additional group of pooled probe oligonucleotides; (i) predicting locations with a labeled probe oligonucleotide, based on pooling information and probe oligonucleotide sequence information; and (j) comparing the detected labels and location information from step (h) with the predicted label location information from step (i), whereas any non-match is indicative of a poor quality of the test oligonucleotide at that location.

Figure 5:
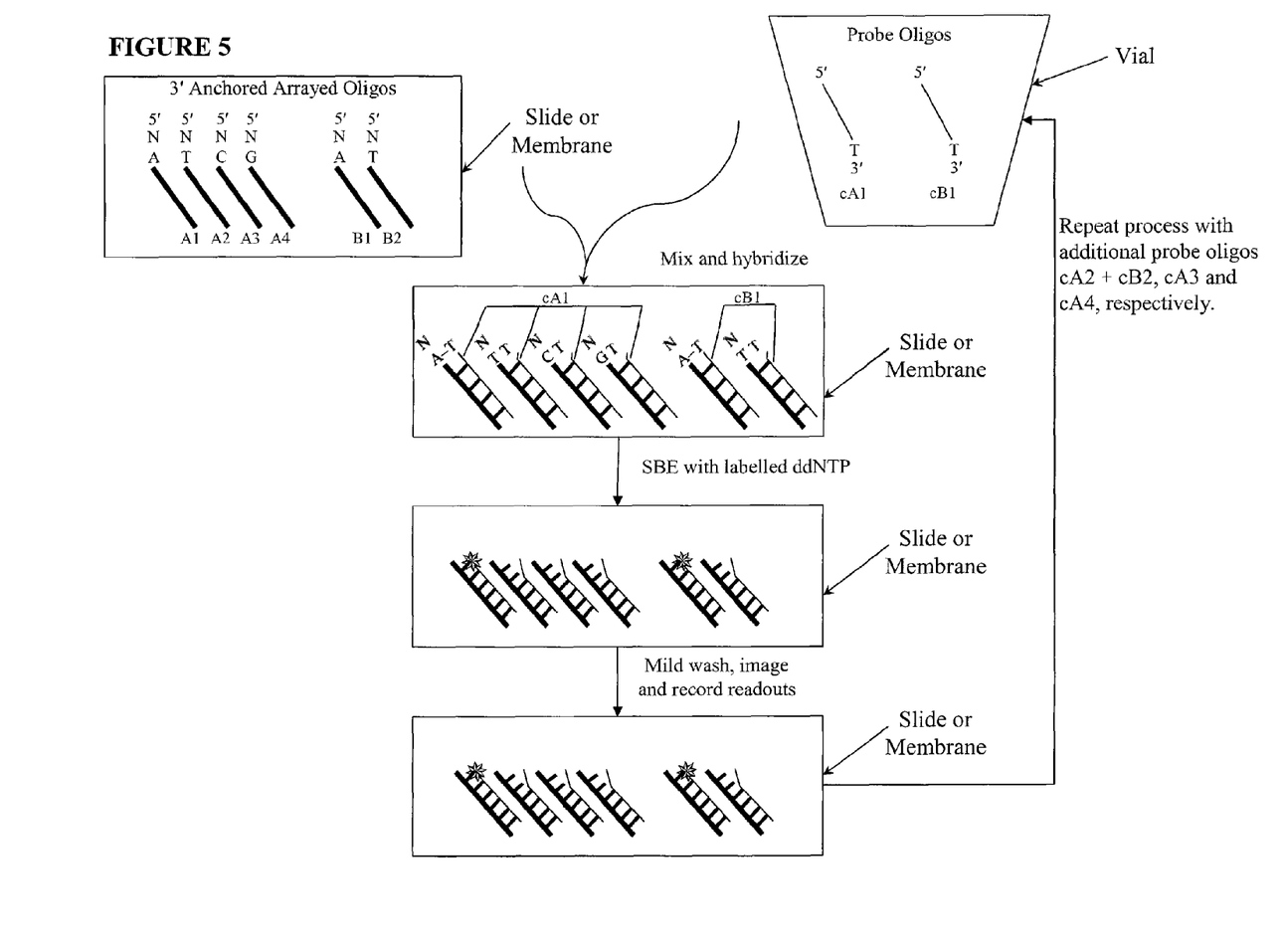
FIG. 5 illustrates yet another scheme for the method of verification of oligonucleotides on a solid support. Arrayed oligonucleotides have their 3' ends anchored to the surface of the slide. The second to last base at the 5' end of the arrayed oligonucleotides is unique and represents each allele (A1-A4, and B1-B2, respectively) of a multi-allelic locus. Arrayed oligonucleotides are only extended at the presence of a perfectly matching probe oligonucleotide.

FIG. 5 provides a schematic drawing of the key steps of this above embodiment. Arrayed oligonucleotides have their 3' ends anchored to the surface of the slide or membrane. The second to last base at the 5' end of the arrayed oligonucleotides is unique and represents each allele (A1-A4, and B1-B2, respectively). Probe oligonucleotides are synthesized that complements each arrayed test oligonucleotide. For a multi-allelic locus, a probe oligonucleotide is synthesized for each allele, with the 3' base being a complement to the unique, second to last base of the arrayed test oligonucleotide. The probe oligonucleotides are groups into at most four groups, with probe oligonucleotides for each allele of a multi-allelic locus separated into a different group. When a group of the probes are mixed with the arrayed test oligonucleotides, each probe only have a perfect match with one of the arrayed test oligonucleotides. In the case of FIG. 5, cA1 hybridizes and has a perfect match with A1, cB1 has a perfect match with B1. Although cA1 might hybridize with A2, A3 or A4, allele specific, single base extension will only extend cA1. The same is true for cB1. A mild wash can be used to get rid of un-incorporated ddNTP, before imaging of the labeled probe oligonucleotides. Imaging results are compared with expected results predicted in silico, to review the quality of the test oligonucleotides. Cycling with the other groups of pooled probe oligonucleotides (cA2 and cB2, cA3, cA4, respectively) allows the imaging and quality control of the other test oligonucleotides.

Although the embodiments and examples above describe the verification of allele specific test oligonucleotides, it is important to stress that the methods also apply to the quality control of any test oligonucleotides, such as those used for gene expression analysis, where most times only a single oligonucleotide is needed for each gene. In fact, the test oligonucleotides do not even need to be used subsequently in a microarray based assay. Any oligonucleotide can be tested by these methods. It is also envisioned that the probe oligonucleotides can be the source of the poor quality as well, although this can easily be ruled out by testing with an additional, newly synthesized probe oligonucleotide. Preferably, the test and probe oligonucleotides are from about 10 to about 100 nucleotides in length, more preferably from about 20 to about 60 nucleotides in length, or from about 20 to about 30 nucleotides in length.

We describe here a couple of prophetic examples where quality analysis is performed on un-related oligonucleotides. By un-related, it is meant that the oligonucleotides are not allelic variants of the same locus, as shown in FIGS. 2-5. These oligonucleotides could be used subsequently for any purpose. Most likely they are used for gene expression based analysis, especially when used as a diagnostics tool. These methods are useful for the quality control of oligonucleotides from a signature set of gene, for certain disease or conditions. As stated earlier, the tested oligonucleotides do not even need to be used in a microarray system.

Figure 6:
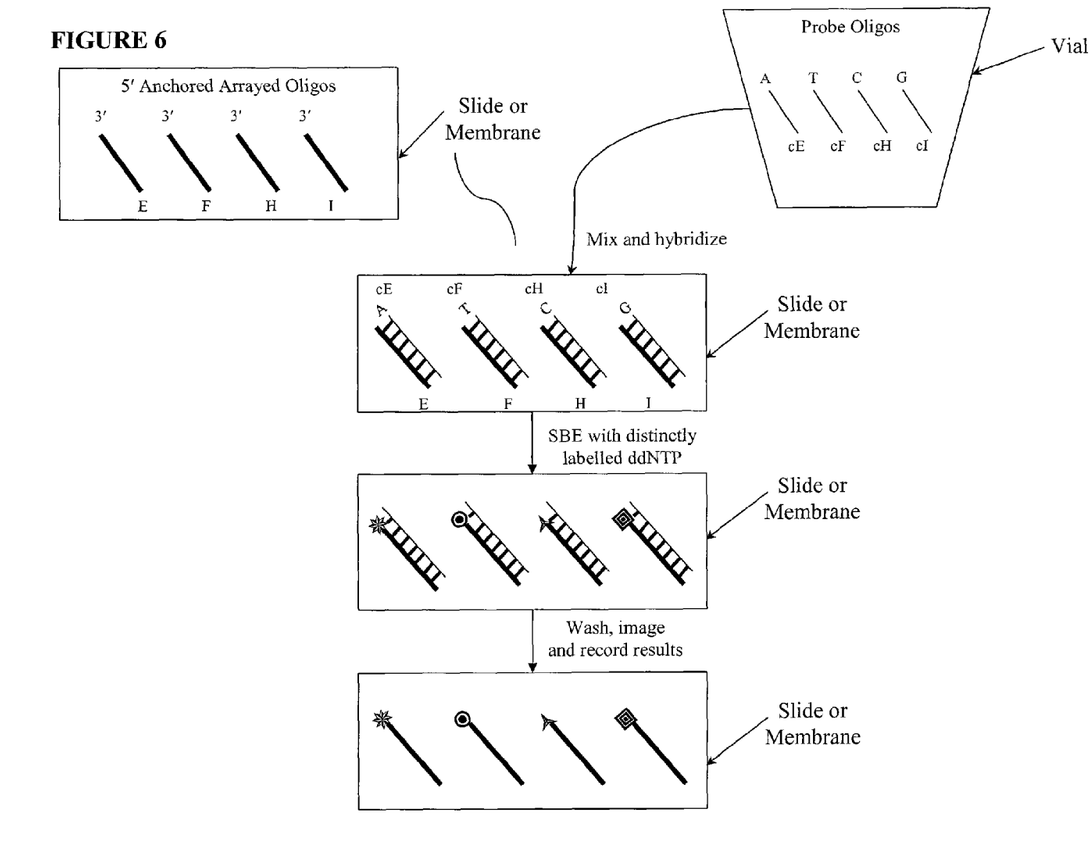
FIG. 6 shows a different example for the quality control of oligonucleotides. Here allele specific oligonucleotides are not considered. Each gene is represented by a single test oligonucleotide on the array. The 5' end of the test oligonucleotides are anchored on the slide. This scheme is useful for quality control of oligonucleotides used in gene expression based analyses.

FIG. 6 shows one of these examples. Here, four 'un-related' oligonucleotides are anchored on the slide via their 5' end (shown as oligonucleotides E, F, H and I), at discrete locations. Four probe oligonucleotides are synthesized. The probes are complements of the test oligonucleotides on the arrays, except each with an extra 5' base (probes cE, cF, cH, cI, with 5' extra bases A, T, C, G, respectively). Hybridization and single base extension with distinctly labeled ddNTP results in distinct label for each test oligonucleotide. If the detected label for a location is in agreement with that of predicted label, the test oligonucleotide is considered of good quality. Although only four test and probe oligonucleotides are shown here, it is obvious that one can expand this to any number of test and probe oligonucleotides. In the cases where more than four oligonucleotides are tested, a good quality test oligonucleotide is one that the detected label matches with the predicted label. Any location where the detected label does not match with that of expected (predicted) label, a potentially poor quality test oligonucleotide is detected.

Figure 7:
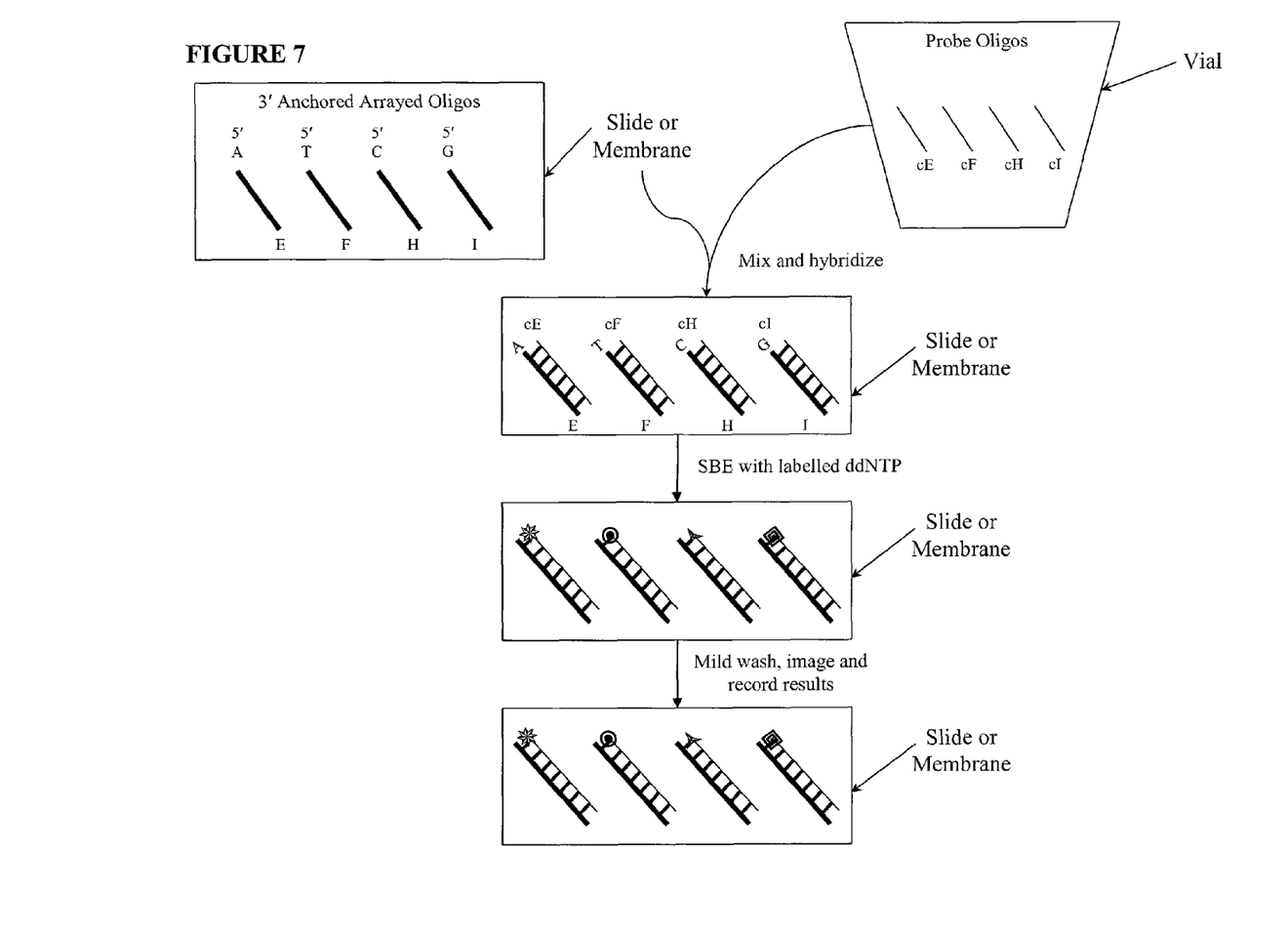
FIG. 7 shows an alternative example for the quality control of oligonucleotides. Here allele specific oligonucleotides are not considered. Each gene is represented by a single test oligonucleotide on the array. The 3' end of the test oligonucleotides are anchored on the slide. This scheme is useful for quality control of oligonucleotides used in gene expression based analyses.

FIG. 7 shows the second of these examples. Here, four 'un-related' oligonucleotides are anchored on the slide or membrane via their 3' end (shown as oligonucleotides E, F, H and I), at discrete locations. Each has a 5' base that is unique from the others (A, T, C, G respectively). Four probe oligonucleotides are synthesized. The probes are complements of the test oligonucleotides on the array, except they are one base short at the 3' end (without a complement to the 5' base of the arrayed test oligonucleotides). Hybridization and single base extension with distinctly labeled ddNTP results in distinct label for each probe oligonucleotide. If the detected label for a location is in agreement with that of a predicted label, the test oligonucleotide is considered of good quality. Although only four test and probe oligonucleotides are shown here, it is obvious that one can expand this to any number of test and probe oligonucleotides. In the cases where more than four oligonucleotides are tested, a good quality test oligonucleotide is one that the detected label matches with the predicted label. Any location where the detected label does not match with that of expected (predicted) label, a potentially poor quality test oligonucleotide is detected.

Nucleic acid hybridization simply involves providing single stranded nucleic acid molecules under conditions where the probe and the complement target can form stable hybrid duplexes through complementary base pairing. The principles, as well as methods of optimizing hybridization conditions, are well known in the field. The method for allele specific single base extension is also well known. For the current methods, the SBE reaction can be optionally cycled a number of times to increase specific probe elongation and thus increase probe spot signal intensity. It is envisioned that single base extension does not occur at the end of which the test oligonucleotides are anchored to the solid support. This is achieved either by the incorporation of a non-matching last base of the probe oligonucleotide, or simply due to the polymerase's failure to access the close to the surface of the solid support.

Specificity and self-extension are two of the common problems associated with a single base extension assay. These were addressed in commonly owned U.S. patent application Ser. No. 10/114,908, now U.S. Pat. No. 6,986,992 (P450 single nucleotide polymorphism biochip analysis), the disclosure of which is hereby incorporated by reference in its entirety.

A number of polymerases can be used for the addition of labeled dideoxy nucleotide to the 3' end of the oligonucleotides, and the optional cycling of reaction. If the probe oligonucleotide used is an RNA oligonucleotide, DNA polymerase I (e.g., T7 DNA polymerase), or reverse transcriptase, can all be used to incorporate a labeled dideoxy nucleotide, to the 3' end of the test oligonucleotide probe in a test/RNA probe complex. While the native enzymes are useful for these reactions, some engineered enzymes offer various advantageous, and could be used as well. When both oligonucleotides are DNA oligonucleotides, most DNA polymerases can be used for the labeling reaction.

Dye or hapten-labeled nucleotides are well known in the art. Alternatively, the nucleotides can be labeled with radioisotopes as well. Detection methods for the dye or hapten labels are also well known. For the purpose of detection associated with the methods of the instant application, any dye/hapten label that is readily detectable can be used. Common labels such as Cynine dyes, IR dyes, Rhodamine dyes, Alexa dyes, and the biotin-streptavidin system are some examples. Since Cy3 and Cy5 dyes are the popular dyes employed in two-color differential gene expression studies, Cy3 or Cy5-ddNTPs are attractive candidates. These methods also offer the flexibility of easily integrating a $3^{rd}$ dye or a $4^{th}$ dye in the rhodamine class. Since labeling is limited to single nucleotide, rate of incorporation is not significantly limited even when structural changes to dye-nucleotide analogs are introduced, an issue which poses difficulty for other methods that rely on incorporation followed by extension.

While some labels are capable of providing a detectable signal directly (e.g., fluorescent dyes), some are through interaction with one or more additional members of a signal production system (e.g., haptens such as biotin-streptavidin). In some instances it is advantageous to use a hapten system. For a biotin-streptavidin system, the ddNTPs are normally biotin-labeled. After SBE reaction of biotin-labeled ddNTP, dye-coupled streptavidin are added and interacts with biotin. Color generated by streptavidin carried dyes is detected by scanning or imaging. While direct labeling of streptavidin is used sometimes for detection of biotin-labeled oligonucleotides, signal amplification is achievable through enzyme based signal amplification. For example, streptavidin could be conjugated with antibodies. Signal could be amplified using antigen conjugated secondary biotin molecules. Dye labeled streptavidin is then used for signal detection. Alternatively, QuantumDot-streptavidin conjugates can be used for signal amplification. Horseradish Peroxidase coupled Streptavidin is another example, this time by chemiluminescent detection.

For the purpose of the current methods, the solid support can be that of a microscope slide, a nitrocellulose membrane, or the like. The surface of a microscope slide can be a planar surface, or a gel polymer coated surface. Additionally, the surface may comprise a plurality of micro-features arranged in spatially discrete regions to produce a texture on the surface, wherein the textured surface provides an increase in surface area as compared to a non-textured surface. The test oligonucleotides are arranged in a microarray format and the detection is by way of scanning or imaging of the microarray on the microscope slide. The test oligonucleotides are either pre-synthesized and attached to the surface of the solid support, or alternatively, the test oligonucleotides are synthesized on the surface by ways such as photolithography. When the test oligonucleotides are synthesized on the surface of the slide, depending on the chemistry used, either the 3' or the 5' end can be attached to the surface.

Means for detecting nucleic acid labels on microarrays are well known to those people skilled in the art. For example, the localization of the label on an array can be accomplished with a microscope. For a fluorescent label, the array can be excited with a light source at the excitation wavelength of the particular label, and the resulting fluorescence detected at the emission wavelength. Scanning and imaging are both common methods for signal detection.

Means for data storage are well know in the software and bioinformatics industry. Numerals software packages have been developed by microarray vendors that can be used to capture the detected signals on a microarray, including the location of each such signals. Database for the storage of these signals, as well as the location and identity (sequence) information of each test oligonucleotide is also well known. The same or a separate database can be used to store information about the probe oligonucleotides. A simple algorithm can be used to perform in silico prediction of locations where and what label will be present, based on test and probe oligonucleotide sequence identity, test nucleotide location information and information on labels of the ddNTP.

In addition to array based platforms, the methods are also applicable to quality testing of oligonucleotides attached to microspheres or beads. The principles for such testing are similar to the array based testing, with the exception that individual oligonucleotides are attached to micro-beads, instead of forming an array on a surface. The beads are uniquely identifiable (e.g., color coded for each bead or each set of beads). Single base extension results in labeling of the hybridized oligonucleotide duplex on the beads, with distinct labels. The combination of the identity of the bead and the label allows the characterization of the oligonucleotides on the beads. The lack of, or unexpected label on a bead or a set of beads is indicative of a poor quality oligonucleotide attached. It is noted that each bead could carry one or more oligonucleotides of the same type. It is also noted that often a set of beads with the same identifiable marker are used, instead of a single bead, for anchoring a distinct test oligonucleotide.

Figure 8:
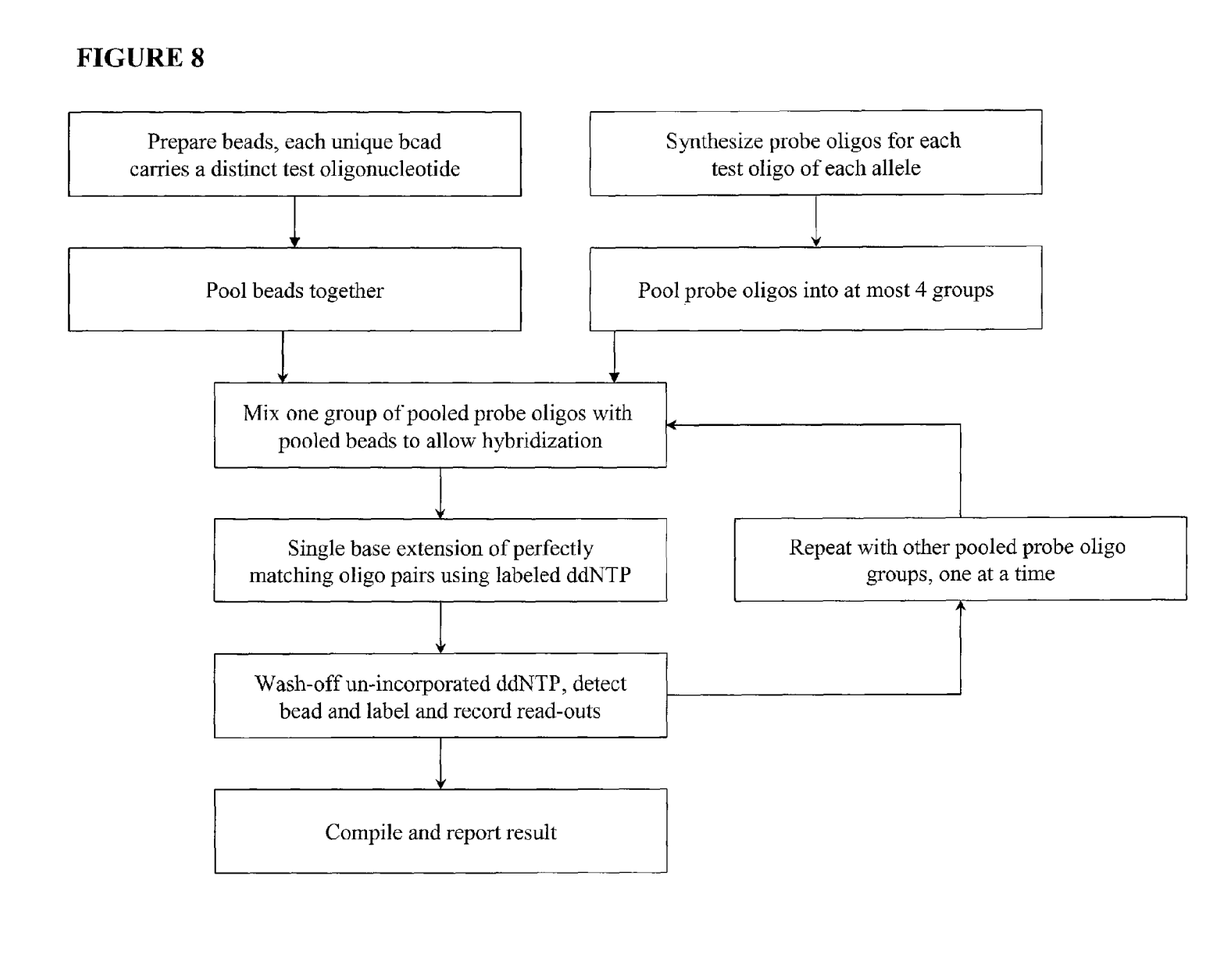
FIG. 8 shows a flow chart for the method of verification of oligonucleotides in a bead based format.

FIG. 8 shows a flow chart for the method of verification of oligonucleotides in a bead based format. Briefly, unique beads are first made; each unique set has a different identifiable marker than the rest. Distinct test oligonucleotides are anchored to each set of unique beads. The beads are then mixed together. In the same time, complementary probe oligonucleotides are synthesized for each test oligonucleotide. These probes are pooled into at most 4 groups, depending upon the number of allelic variants one needs to test. The pooled probes are mixed with the mixture of beads to allow hybridization of the probe and test oligonucleotides. Then, single base extension of perfectly matching oligonucleotide pairs adds a distinct labeled from the labeled ddNTP. Un-incorporated ddNTP can be washed off and the beads and label are then detected. The results are compiled and compared to the expected result. The hybridization-reaction steps are repeated with each group of pooled oligonucleotides. Any deviation from the expected results is indicative of a poor quality oligonucleotide.

The XMAP® technology from Luminex is a platform that could be used for bead based quality control of oligonucleotides. The technology offers color-codes tiny beads, called microspheres, with up to 100 distinct sets. Each set of the beads are 5.6 micron polystyrene microspheres internally dyed with red and infrared fluorophores. Each bead set can be coated with a unique oligonucleotide, allowing the SBE labeling and detection. Within the Luminex 100 compact analyzer, lasers excite the internal dyes that identify each microsphere particle, and also the dye label from the SBE extension. Many readings are made on each bead set, further validating the results. In this way, XMAP® technology allows multiplexing of up to 100 unique assays within a single sample, both rapidly and precisely.

The methods are preferably used for quality control of oligonucleotides for a set of genes/loci of interest. This could be any set of genes/loci from an organism, or more likely a signature set of genes/loci for a condition or trait. It is now known that there are signature sets of genes/loci the expression or allelic information of which are indicative of a human disease or condition, such as cancer, or metabolism of certain molecules and drugs. Measuring gene expression, and identifying allelic information, of these signature sets from an individual suspected of carrying a disease or condition leads to the diagnosis of the disease or condition, provided that the expression levels, or the allelic information, of said signature set of genes are compared to a predetermined control signature related to the disease or condition. These methods are also useful for gene profiling of toxicogenomics studies and preclinical studies of model organisms, as well as animal diseases.

Having described the particular, desired embodiments of the invention herein, it should be appreciated that modifications may be made therethrough without departing from the contemplated scope of the invention. The true scope of the invention is set forth in the claims appended hereto.

What is claimed is:

1. A method for identifying poor quality oligonucleotides on a solid support, comprising:
   (a) preparing an array of test oligonucleotides on the solid support, whereas each of said test oligonucleotides is anchored at the 5' end and occupies a predetermined location on said solid support, and whereas test oligonucleotides from each allele of a multi-allelic locus occupies a separate location and the last base at the 3' end is unique to said allele of the multi-allelic locus;
   (b) synthesizing probe oligonucleotides for each arrayed test oligonucleotide, said probe oligonucleotides being a complement of the arrayed test oligonucleotide and contain one additional base at the 5' end;
   (c) pooling said probe oligonucleotides into at most four groups, wherein probe oligonucleotides representing each allele of a multi-allelic locus is separated into a different group;
   (d) mixing one group of pooled probe oligonucleotides with said arrayed test oligonucleotides to allow hybridization of probe and test oligonucleotides on said solid support;
   (e) performing single base extension reaction with labeled dideoxynucleotides, wherein extension occurs only for those test oligonucleotides having a 3' base that hybridizes with a probe oligonucleotide;
   (f) washing off dideoxynucleotides not incorporated into test oligonucleotides;
   (g) detecting labels on extended test oligonucleotides and their location;
   (h) repeating steps step (d) through step (g) for each additional group of pooled probe oligonucleotides;
   (i) predicting locations of each labeled test oligonucleotide of interest, based on pooling information and probe oligonucleotide sequence information; and
   (j) comparing said detected labels and location information from step (h) with the predicted test oligonucleotide location information from step (i), whereas any non-match is indicative of a poor quality of the test oligonucleotide at that location;
   wherein all the probe oligonucleotides within each group contain the same said additional base such that only a single type of labeled dideoxynucleotide is added for the single nucleotide extension reaction.

2. A method for identifying poor quality oligonucleotides on a solid support, comprising:
   (a) preparing an array of test oligonucleotides on the solid support, whereas each of said test oligonucleotides is anchored at the 3' end and occupies a predetermined location on said solid support, and whereas test oligonucleotides from each allele of a multi-allelic locus occupies a separate location and the second to last base at the 5' end is unique to said allele of the multi-allelic locus;
   (b) synthesizing probe oligonucleotides for each arrayed test oligonucleotide, said probe oligonucleotides being a complement of the arrayed test oligonucleotide and the 3' last base is a complement to the unique base at the second to last position of the 5' end of the arrayed test oligonucleotide;
   (c) pooling said probe oligonucleotides into at most four groups, wherein probe oligonucleotides representing each allele of a multi-allelic locus is separated into a different group;
   (d) mixing one group of pooled probe oligonucleotides with said arrayed test oligonucleotides to allow hybridization of probe and test oligonucleotides on said solid support;
   (e) performing single base extension reaction with labeled dideoxynucleotides, wherein extension occurs only on those probe oligonucleotides the 3' end of which match perfectly with the second base at the 5' end of said arrayed test oligonucleotide;
   (f) washing off dideoxynucleotides not incorporated into probe oligonucleotides;
   (g) detecting labels on extended probe oligonucleotides and their location;
   (h) repeating steps step (d) through step (g) for each additional group of pooled probe oligonucleotides;
   (i) predicting locations with a labeled probe oligonucleotide, based on pooling information and probe oligonucleotide sequence information; and
   (j) comparing said detected labels and location information from step (h) with the predicted label location information from step (i), whereas any non-match is indicative of a poor quality of the test oligonucleotide at that location;
   wherein all the test oligonucleotides contain the same base at the 5' end and a single type of labeled dideoxynucleotide with a complement base is added for the single nucleotide extension reaction.

3. The method according to claim 1 or 2, wherein said labeled dideoxynucleotides contain a biotin label.

4. The method according to claim 1 or 2, wherein said labeled dideoxynucleotides contain a fluorescent dye label.

5. The method according to claim 1 or 2, wherein said arrayed test oligonucleotides are from a signature set of genes the expression or polymorphism of which is indicative of a human disease or condition.

6. The method according to claim 1 or 2, wherein said arrayed test oligonucleotides are from a signature set of genes the expression or polymorphism of which is indicative of a toxicological response.

7. The method according to claim 3, wherein said detecting step further includes a signal amplification step using streptavidin-conjugates.

* * * * *